(12) United States Patent
Fleming

(10) Patent No.: US 8,486,087 B2
(45) Date of Patent: Jul. 16, 2013

(54) SYSTEM AND METHOD FOR REMOVING EXCISED TISSUE

(75) Inventor: Alistair Ian Fleming, Lower Cambourne (GB)

(73) Assignee: Covidien LP, Mansfield, MA (US)

( * ) Notice: Subject to any disclaimer, the term of this patent is extended or adjusted under 35 U.S.C. 154(b) by 249 days.

(21) Appl. No.: 13/093,143

(22) Filed: Apr. 25, 2011

(65) Prior Publication Data

US 2011/0270265 A1 Nov. 3, 2011

Related U.S. Application Data

(60) Provisional application No. 61/330,488, filed on May 3, 2010.

(51) Int. Cl.
*A61B 17/221* (2006.01)

(52) U.S. Cl.
USPC .......................................................... 606/114

(58) Field of Classification Search
USPC .................. 606/110–115, 127, 128; 604/540; 600/562–564
See application file for complete search history.

(56) References Cited

U.S. PATENT DOCUMENTS

| | | | |
|---|---|---|---|
| 30,471 A | 10/1860 | Dudley | |
| 35,164 A | 5/1862 | Logan et al. | |
| 156,477 A | 11/1874 | Bradford | |
| 1,609,014 A | 11/1926 | Dowd | |
| 3,800,781 A | 4/1974 | Zalucki | |
| 4,557,255 A | 12/1985 | Goodman | |
| 4,744,363 A | 5/1988 | Hasson | |
| 4,790,812 A | 12/1988 | Hawkins, Jr. et al. | |
| 4,927,427 A | 5/1990 | Kriauciunas et al. | |
| 4,997,435 A | 3/1991 | Demeter | |
| 5,037,379 A | 8/1991 | Clayman et al. | |
| 5,074,867 A | 12/1991 | Wilk | |
| 5,084,054 A | 1/1992 | Bencini et al. | |
| 5,143,082 A | 9/1992 | Kindberg et al. | |
| 5,176,687 A | 1/1993 | Hasson et al. | |
| 5,190,542 A | 3/1993 | Nakao et al. | |
| 5,190,555 A | 3/1993 | Wetter et al. | |
| 5,192,284 A | 3/1993 | Pleatman | |
| 5,192,286 A | 3/1993 | Phan et al. | |
| 5,201,740 A | 4/1993 | Nakao et al. | |
| 5,215,521 A | 6/1993 | Cochran et al. | |
| 5,234,439 A | 8/1993 | Wilk et al. | |
| 5,279,539 A | 1/1994 | Bohan et al. | |

(Continued)

FOREIGN PATENT DOCUMENTS

| | | |
|---|---|---|
| EP | 0 791 330 | 8/1997 |
| WO | WO 93/15675 | 8/1993 |
| WO | WO 2004/002334 | 1/2004 |

OTHER PUBLICATIONS

European Search Report EP 06 00 5182, dated Jun. 13, 2006.

*Primary Examiner* — Ryan Severson

(57) ABSTRACT

A method and system for removing tissue from a body cavity is provided. The system includes a retrieval bag that is insertable through a first incision in tissue and includes open and closed ends. A surgical instrument is insertable into the body cavity and configured to grasp and excise a sample/specimen from within the body cavity and selectively substantially seal the retrieval bag. A fluid circulator in fluid communication with the surgical instrument and the open end of the retrieval bag is configured to evacuate gaseous matter from within the body cavity and into the open end of the retrieval bag such that the retrieval bag substantially encircles the excised tissue specimen.

19 Claims, 4 Drawing Sheets

U.S. PATENT DOCUMENTS

| | | | |
|---|---|---|---|
| 5,312,416 A | 5/1994 | Spaeth et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,465,731 A | 11/1995 | Bell et al. |
| 5,465,732 A | 11/1995 | Abele |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,643,283 A | 7/1997 | Younker |
| 5,645,083 A | 7/1997 | Essig et al. |
| 5,647,372 A | 7/1997 | Tovey et al. |
| 5,658,296 A | 8/1997 | Bates et al. |
| 5,679,423 A | 10/1997 | Shah |
| 5,681,324 A | 10/1997 | Kammerer et al. |
| 5,735,289 A | 4/1998 | Pfeffer et al. |
| 5,755,724 A | 5/1998 | Yoon |
| 5,759,187 A | 6/1998 | Nakao et al. |
| 5,769,794 A | 6/1998 | Conlan et al. |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,836,953 A | 11/1998 | Yoon |
| 5,853,374 A | 12/1998 | Hart et al. |
| 5,895,392 A | 4/1999 | Riek et al. |
| 5,906,621 A | 5/1999 | Secrest et al. |
| 5,957,884 A | 9/1999 | Hooven et al. |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,036,681 A | 3/2000 | Hooven |
| 6,123,701 A | 9/2000 | Nezhat |
| 6,152,932 A | 11/2000 | Ternström |
| 6,162,235 A | 12/2000 | Vaitekunas |
| 6,165,121 A | 12/2000 | Alferness |
| 6,168,603 B1 | 1/2001 | Leslie et al. |
| 6,228,095 B1 | 5/2001 | Dennis |
| 6,277,083 B1 | 8/2001 | Eggers et al. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,383,196 B1 | 5/2002 | Leslie et al. |
| 6,383,197 B1 | 5/2002 | Conlon et al. |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,872,211 B2 | 3/2005 | White et al. |
| 6,887,255 B2 | 5/2005 | Shimm |

SYSTEM AND METHOD FOR REMOVING EXCISED TISSUE

This application claims priority from provisional application Ser. No. 61/330,488, filed May 3, 2010, the entire contents of which are incorporated herein by reference.

BACKGROUND

1. Technical Field

The present disclosure relates to a system and method for removing excised tissue and, more particularly, to a system and method that utilizes a surgical retrieval bag that is configured for the removal of excised tissue from an endoscopically accessed surgical environment.

2. Background of Related Art

Laparoscopic and endoscopic surgical procedures are minimally invasive procedures in which operations are carried out within the body by using elongated instruments inserted through small entrance openings in the body. The initial opening in the body tissue configured to allow passage of the endoscopic or laparoscopic instruments to the interior of the body may be a natural passageway of the body, or it can be created by a tissue piercing instrument such as a trocar, scalpel, or the like.

Minimally invasive procedures may be used for partial or total removal of body tissue or organs from the interior of the body, e.g. nephrectomy, cholecystectomy, and other procedures including thoracic procedures. During such procedures, it is common that a cyst, tumor, or other affected tissue or organ must be removed via the access opening in the skin, or through a cannula. Various types of entrapment devices e.g., retrieval bag or sack, have been disclosed to facilitate this procedure.

Problems typically associated with removing excised tissue are grave when dealing with infected or tumorous tissue. For example, when removing infected or tumorous tissue there exists the possibility of seeding the cells associated with infected or tumorous tissue to other sites, and care must be exercised to avoid contacting the excised tissue with surrounding tissue. This is particularly difficult when removing large amounts of tissue or large sized organs through a relatively small incision.

Also, in minimally invasive surgical procedures, access to target tissue is limited as is maneuverability of the instrument within the cavity. It can also be difficult to remove large specimens through the small incisions Thus, it would be advantageous to provide a system and method that is configured to remove excised tissue from a minimally invasively accessed surgical environment while reducing the likelihood of seeding cancerous cells to surrounding tissue and maintaining the integrity of the excised tissue when the excised tissue is placed in the retrieval bag and the retrieval bag is being removed from the surgical environment.

SUMMARY

The present disclosure provides in one aspect a system configured for removing tissue from a body cavity. The system includes a retrieval bag that is insertable through a first incision in tissue. The retrieval bag includes an open end and a closed end. A surgical instrument is insertable into the body cavity to grasp and excise a tissue specimen from within the body cavity and selectively substantially seal the retrieval bag. A fluid circulator in fluid communication with the surgical instrument and the open end of the retrieval bag is configured to evacuate gaseous matter from within the body cavity and into the open end of the retrieval bag such that the retrieval bag substantially encircles the excised tissue specimen.

In some embodiments, the retrieval bag includes a textured surface configured to facilitate maintaining the tissue specimen in a substantially fixed position during the evacuation of gaseous matter from within the body cavity.

In some embodiments, one of the surgical instrument and fluid circulator is in fluid communication with the retrieval bag via a fluid conduit.

The surgical instrument can in some embodiments be an endoscopic forceps. In some embodiments, the surgical instrument can include a cutting element that is configured to excise the tissue specimen and sever the retrieval bag subsequent to the placing of the tissue specimen therein and the sealing thereof.

The present disclosure provides in another aspect a method for removing tissue from a body cavity of a patient. The method includes forming at least one incision in tissue to access the body cavity. After the incision(s) are formed, a retrieval bag is inserted though one of the incisions and into the body cavity adjacent a tissue specimen. Gaseous matter is evacuated from the body cavity and the retrieval bag is inflated with the evacuated gaseous matter such that the retrieval bag substantially encircles the tissue specimen. A portion of the retrieval bag is substantially sealed around the tissue specimen such that the sealed portion of the retrieval bag separates from the rest of the retrieval bag. The sealed portion of the retrieval bag including the tissue specimen contained therein is removed from the body cavity.

In some embodiments, the step of substantially sealing a portion of the retrieval bag includes inserting a sealing instrument into the retrieval bag.

In some embodiments, the step of substantially sealing a portion of the retrieval bag further includes the step of translating a cutting element through the sealed portion of the retrieval bag.

In some embodiments, prior to the step of inserting the retrieval bag, the tissue specimen is excised. In some embodiments, the step of excising the tissue specimen includes excising tissue that is located within a thoracic cavity of a patient.

In some embodiments, the step of evacuating gaseous matter includes the step of introducing a surgical instrument that is operably associated with a fluid circulator and in fluid communication with the retrieval bag into the incision that is not occupied by the retrieval bag.

In some embodiments, the step of inserting the retrieval bag includes inserting a retrieval bag that includes a textured surface, wherein the textured surface is configured to facilitate maintaining the tissue specimen in a substantially fixed position during the evacuation step.

BRIEF DESCRIPTION OF THE DRAWINGS

Embodiments of the presently disclosed specimen retrieval apparatus are described hereinbelow with reference to the drawings wherein.

DETAILED DESCRIPTION OF THE EMBODIMENTS

Figure 1:
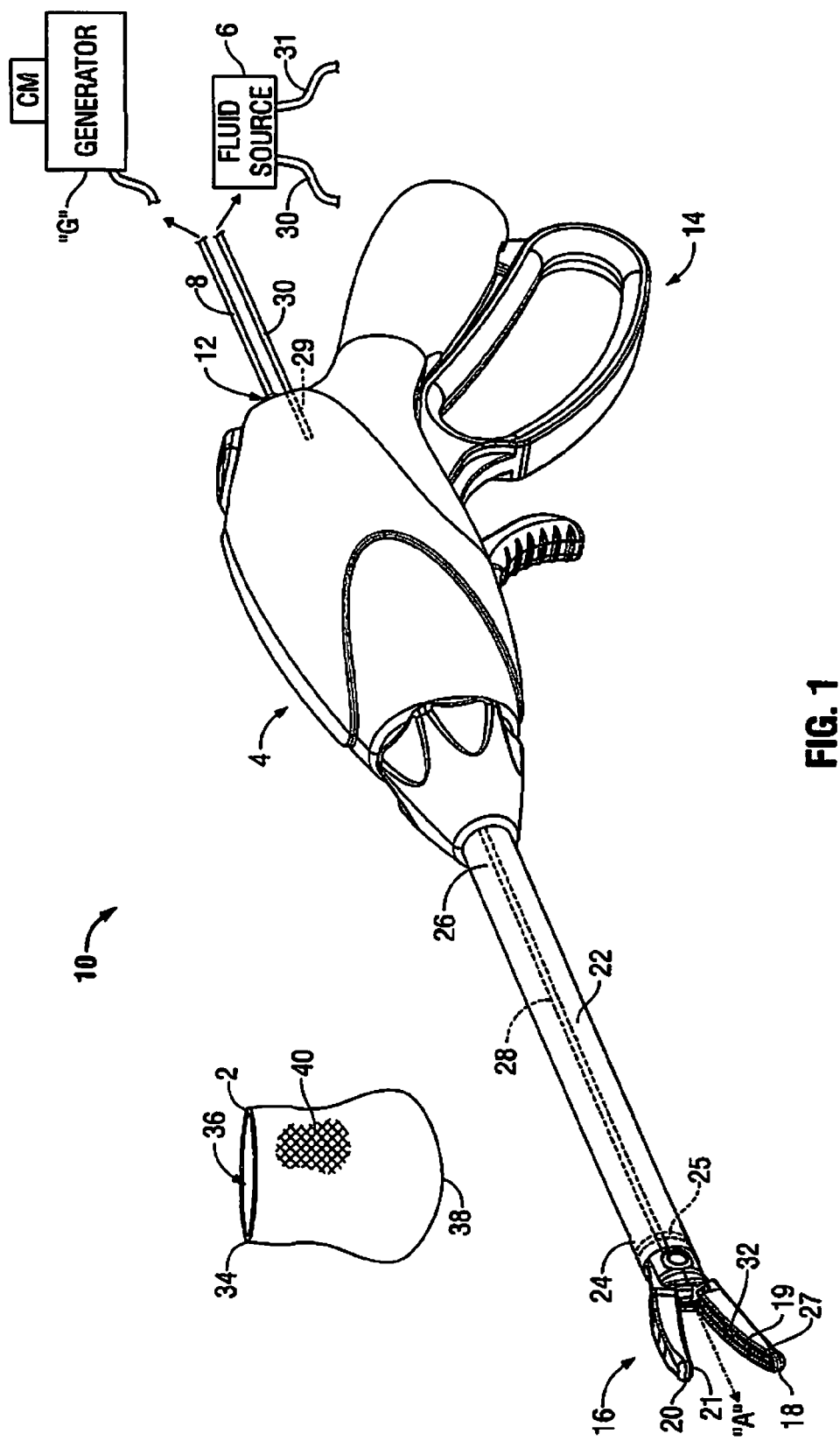
FIG. 1 is a perspective view of a system for removing tissue from a body cavity according to an embodiment of the present disclosure.

Embodiments of the present disclosure will now be described in detail with reference to the drawings, in which like reference numerals designate identical or corresponding elements in each of the several views. As used herein, the term distal refers to the portion of the instrument which is further from the user while, the term proximal refers to that portion of the instrument which is closer to the user. In the following description, well-known functions or constructions are not described in detail to avoid obscuring the present disclosure in unnecessary detail.

As used herein with reference to the present disclosure, the terms laparoscopic and endoscopic refer to instruments having a relatively narrow operating portion for insertion into a cannula or a small incision in the skin. They also refer to minimally invasive surgical procedures. It is believed that the present disclosure may find use in any procedure where access to the interior of the body is limited to a relatively small incision, with or without the use of a cannula as in minimally invasive procedures. The devices herein may find particular use in minimally invasive thoracic surgery where access to the thoracic cavity is through a space located between adjacent ribs known as the intercostal space.

Figure 2A:
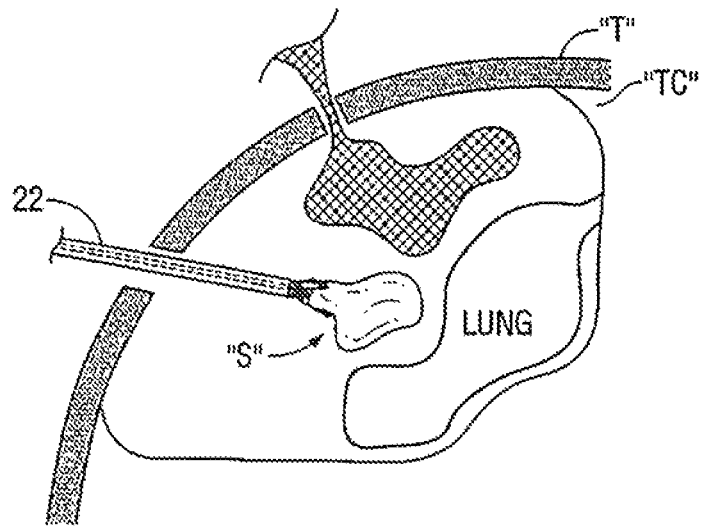
FIGS. 2A-2D are perspective views illustrating a method of use of the system depicted in FIG. 1.
Figure 2B:
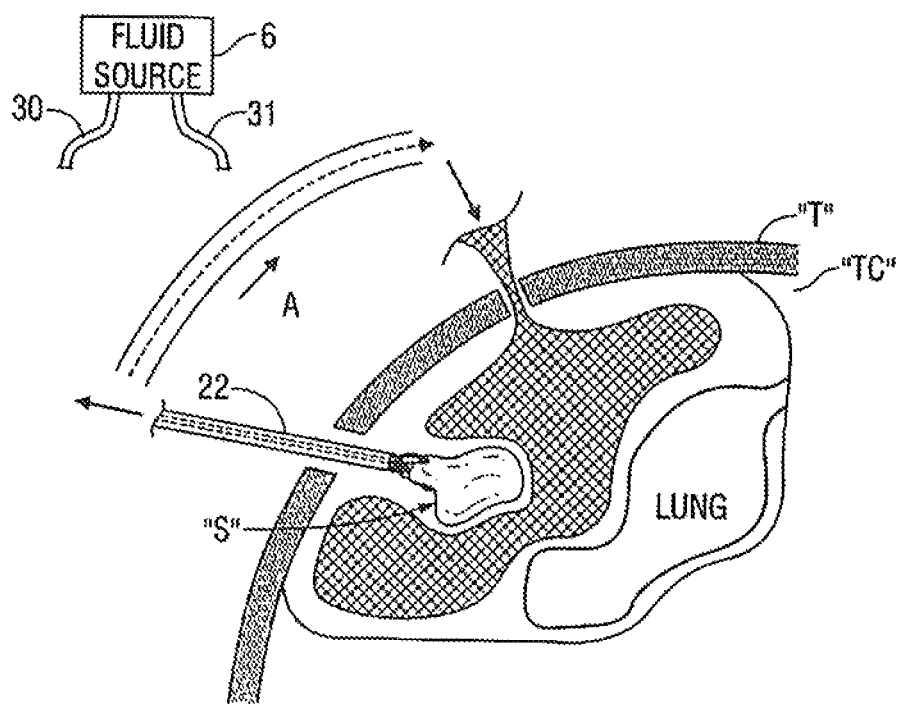
Figure 2C:
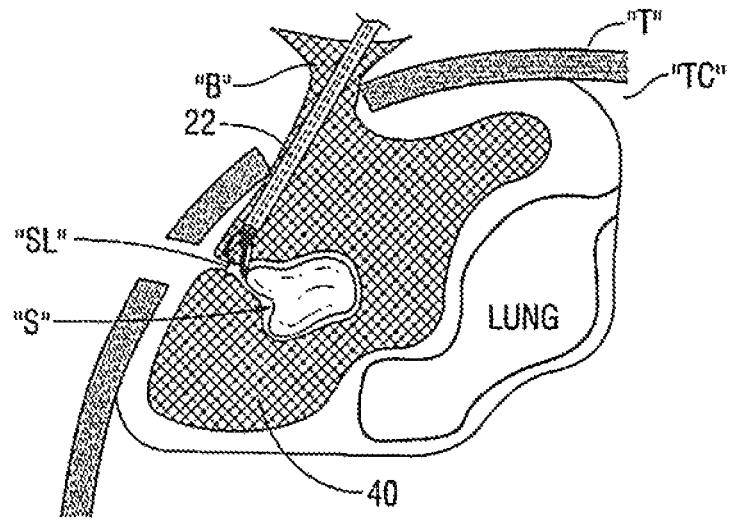
Figure 2D:
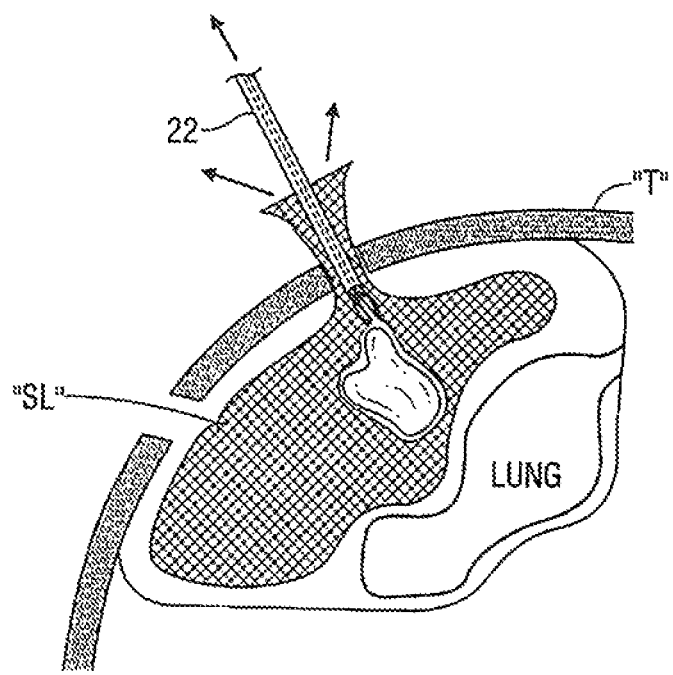
Figure 3:
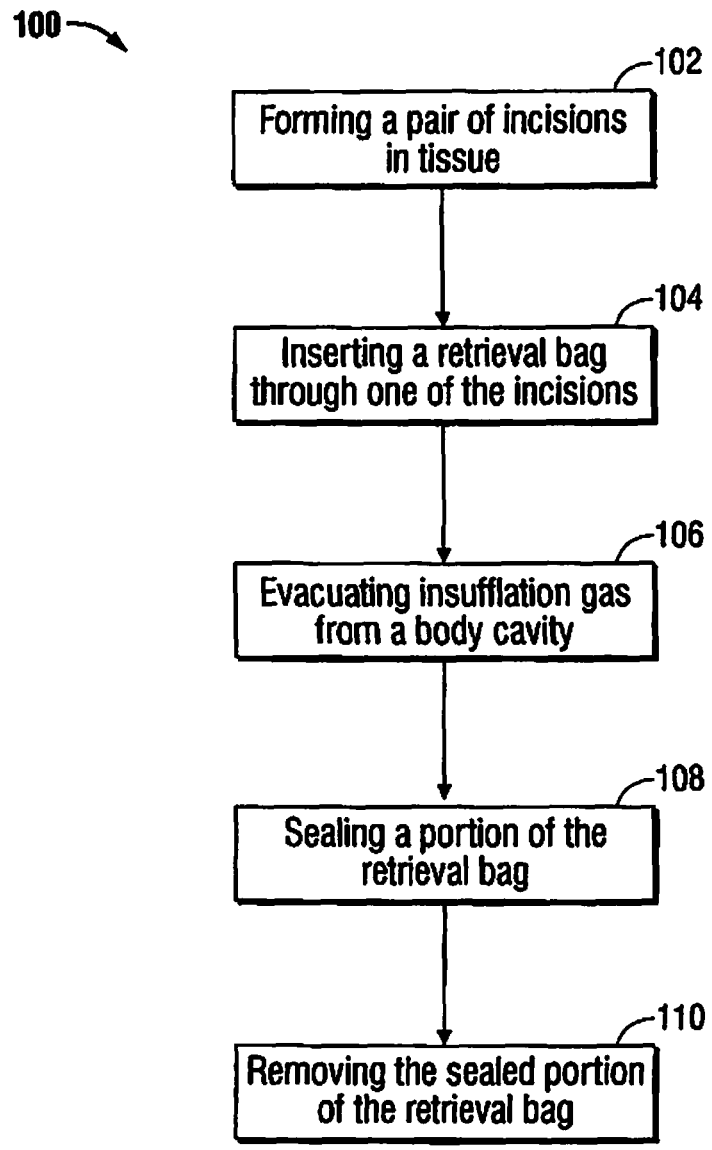
FIG. 3 is a flowchart illustrating the steps of the method of use depicted in FIGS. 2A-2D.

With reference to FIGS. 1-3, a system 10 and method 100 of use of the same for removing a sample/specimen "S" from a body cavity of a patient is illustrated. In the description that follows, and for illustrative purposes, the body cavity is a thoracic body cavity "TC" of a patient. System 10 includes a retrieval bag 2, a surgical instrument 4 that is operably coupled to an energy source (e.g., a generator "G"), and a fluid source or circulator 6.

With reference to FIG. 1, a surgical instrument 4 is illustrated. Surgical instrument 4 is configured for insertion through an incision in tissue and configured to grasp and excise a tissue sample/specimen "S" from within thoracic body cavity "TC." In the illustrated embodiment, surgical instrument 4 can also optionally be configured to substantially selectively seal the retrieval bag 2. One type of surgical instrument 4 that may be utilized with the system 10 and method 100 of the present disclosure is an electrosurgical apparatus, e.g., an endoscopic electrosurgical forceps 4. As can be appreciated, the retrieval bag can be fully sealed or substantially sealed, provided it is closed off sufficiently to prevent seeding of cancerous tissue.

Briefly, forceps 4 is shown configured for use with various electrosurgical procedures and generally includes a housing 12, electrosurgical cable 8 that connects the forceps 4 to a source of electrosurgical energy (e.g., electrosurgical generator "G"), a handle assembly 14, a drive assembly (not shown), and an end effector assembly 16 that operatively connects to a drive rod (not shown) of the drive assembly. The drive assembly is in operative communication with handle assembly 14 for imparting movement of one or both of a pair of jaw members 18, 20 (FIG. 1) associated with the end effector assembly 16. Jaw members 18 and 20 are configured to mutually cooperate to grasp and seal tissue specimens (see FIG. 2A, for example). In the illustrated embodiment, jaw members 18 and 20 are configured to seal (or substantially seal) the retrieval bag 2 (or portion thereof) subsequent to a sample/specimen "S" being positioned adjacent to or placed into the retrieval bag 2 (see FIGS. 2C and 2D where the seal is represented by "SL"); described in greater detail below. To facilitate sealing the retrieval bag 2, one or both of respective seal surfaces 19 and 21 of the jaw members 18 and 20 may be coated with a lubricous material, e.g., TEFLON®. In the illustrated embodiment, seal surface 19 of jaw member 18 is coated with a layer of TEFLON® which is represented by hatching 32. A shaft 22 includes a distal end 24 that is configured to mechanically engage the end effector assembly 16 and a proximal end 26 that mechanically engages the housing 12.

In the illustrated embodiment, a cutting element 25 (shown in phantom in FIG. 1) is operably disposed at the distal end 24 of the shaft 22 and is movable through a longitudinal cutting channel 27 that is operably disposed through one or both of the jaw members, e.g., jaw member 18. Cutting element 25 is configured to sever tissue and/or a portion, e.g., a sealed portion, of the retrieval bag 2. A lumen 28 (shown in phantom in FIG. 1) in fluid communication with fluid circulator 6 via a fluid conduit, e.g., a return hose 30, extends internally along a length of the shaft 22 and is configured to evacuate air from the thoracic body cavity "TC". In the illustrated embodiment, a connection hub 29 (shown in phantom in FIG. 1) operably disposed at a proximal end of housing 12 and within the housing 12 provides an intermediary interface between the return hose 30 and the lumen 28. One or more suitable fluid conduits (not explicitly shown) may extend within the housing 12 and provide fluid communication between the hub 29 and lumen 28.

In the illustrated embodiment, forceps 4 is operatively and selectively coupled to an electrosurgical generator "G" for performing an electrosurgical procedure. The generator "G" may be configured for monopolar and/or bipolar modes of operation. The generator "G" may include or is in operative communication with a system (not shown) that may include one or more processors in operative communication with one or more control modules ("CM") that are executable on the processor. The control module may be configured to instruct one or more modules to transmit electrosurgical energy, which may be in the form of a wave or signal/pulse, via one or more cables (e.g., an electrosurgical cable 8) to the forceps 4. In the illustrated embodiment, the generator "G" and/or the control module "CM" is configured to provide electrosurgical energy that is capable of excising a sample/specimen "S" and sealing (or substantially sealing) the retrieval bag 2, or portion thereof.

For a more detailed description of the forceps 4 including handle assembly 14, the drive assembly, end effector 16 including jaw members 16 and 18, cutting element 25 (and operative components associated therewith) and electrosurgical cable 8 (including line-feed configurations and/or connections), reference is made to commonly-owned U.S. patent application Ser. No. 11/595,194, now U.S. Patent Publication No. 2007-0173814, which was filed on Nov. 9, 2006 and is incorporated by reference herein in its entirely.

With continued reference to FIG. 1, retrieval bag 2 is shown. Retrieval bag 2 is insertable within an incision in tissue (see FIG. 2A, for example). Retrieval bag 2 may be made from any suitable material. In the illustrated embodiment, retrieval bag 2 is made from an elastomeric, bio-compatible material that is substantially impervious to bodily fluids. Retrieval bag 2 includes an open end 34 with an opening 36 of suitable proportion and a closed end 38. Opening 36 may function as a fluid channel and is configured to operably couple to the fluid circulator 6. More particularly, opening 36 is configured to operably couple, via any suitable coupling method, to a fluid conduit, e.g., a fluid supply hose 31, operably associated with the fluid circulator 6. One suitable coupling method that may be utilized in coupling the fluid supply hose 31 of the fluid circulator 6 to the opening 38 is the "Luer-Lok" or "Luer Slip" coupling method. In the illustrated embodiment, a portion of the retrieval bag 2 is configured to facilitate maintaining the sample/specimen "S" in a substantially fixed position during evacuation of the thoracic cavity "TC." More particularly, a portion 40 of an internal surface of the retrieval bag 2 may be textured or otherwise configured to maintain the sample/specimen "S" in a substantially fixed position during evacuation of the thoracic cavity "TC." In certain instances, it may prove useful not to have a textured portion on the internal surface associated with the retrieval bag 2.

Fluid circulator 6 may be any suitable fluid circulator known in the art, e.g., a manual hand-held fluid circulator, an electrically powered fluid circulator, etc. In the illustrated embodiment, fluid circulator is an electrically powered fluid circulator 6. Fluid circulator 6 operably and removably couples to the forceps 4 and is in fluid communication with the lumen 28 associated therewith via return hose 30. Fluid circulator 6 is configured to evacuate air from within the thoracic cavity "TC" and into the open end 34 of the retrieval bag 2 such that the retrieval bag 2 forms a "shrink-wrap" substantially around (or otherwise encircles) the excised sample/specimen "S", as best seen in FIG. 2C. More particularly, the air that is evacuated from within the thoracic cavity "TC" is pumped into the retrieval bag 2. This pumping of the air into the retrieval bag 2 creates an equi-pressure that forms the "shrink-wrap" around the excised sample/specimen "S." That is, the pressure of the retrieval bag 2 and the thoracic cavity "TC" will be equal to one another, which, in turn, causes the "shrink-wrap" to form substantially around the excised sample/specimen "S."

In certain procedures, e.g. laparoscopic procedures, the fluid circulator 6 may be configured to insufflate the abdominal cavity or other area located within a patient. In this instance, the return hose 30 may serve as both a supply hose and a return hose 30.

With reference to FIGS. 2A-2D and FIG. 3, a method 100 of use of system 10 is now described in terms of removing tissue from a body cavity of a patient. As noted above, the body cavity may be, for example, the thoracic cavity of a patient. Initially, one or more suitable instruments, e.g., trocar, scalpel, or the like, are utilized to create one or more incisions in tissue of a patient. For illustrative purposes, two incisions, a first incision that is sized to receive the retrieval bag 2 (or portion thereof) and a second incision that is sized to receive the forceps 4, are shown, see FIG. 3 at step 102.

Subsequently, the forceps 4 is utilized to excise and grasp a sample/specimen "S," e.g., a portion of a lung, FIG. 2A. Retrieval bag 2 is inserted into the first incision adjacent the excised sample/specimen "S," see FIG. 2A and FIG. 3 at step 104. Supply hose 31 is coupled to the opening 36 of the retrieval bag 2 and the air within the thoracic cavity "TC" is evacuated therefrom via the fluid circulator 6 and pumped into the retrieval bag 2 forming a "shrink-wrap" substantially around the excised sample/specimen "S," see FIG. 2B and FIG. 3 at step 106. An advantage of maintaining equipressure in some embodiments is it prevents the lung from re-expanding (in thoracic procedures) or prevents loss of pneumoperitoneum (in laparoscopic procedures). For illustrative purposes, this "pumping" action is illustrated by directional vector arrow $\vec{A}$.

In one particular embodiment, forceps 4 is removed from the second incision and inserted into the retrieval bag 2 that has been previously inserted into the first incision. In this instance, the forceps 4 is able to seal the retrieval bag from the inside. With the jaw members 18 and 20 in an open configuration, a portion of the retrieval bag 2 is positioned therebetween such that the respective seal surfaces 19 and 21 are in contact with the retrieval bag 2.

Generator "G" in this embodiment is activated and electrosurgical energy is supplied to the seal surface 19 and 21 of the jaw members 18 and 20 such that the portion of the retrieval bag 2 that is positioned between the jaw members 18 and 20 is sealed, see FIG. 2C and FIG. 3 at step 108. In one particular instance, the cutting element 25 may be utilized to sever the sealed portion of the retrieval bag 2 from the rest of the retrieval bag 2. Alternatively, the generator "G" and/or control module "CM" may be configured to provide electrosurgical energy to the seal surfaces 19 and 21 capable of sealing and separating the sealed portion of the retrieval bag 2 from the rest of the retrieval bag 2. The "shrink-wrapped" portion of the retrieval bag 2 substantially around the excised sample/specimen "S" is removed from the thoracic cavity "TC" through the first incision FIG. 2D and FIG. 3 at step 110. During removal of the "shrink-wrapped" portion of the retrieval bag 2 substantially around the excised sample/specimen "S," the remainder of the retrieval bag 2 remains substantially in place and provides an additional barrier of protection for tissue adjacent the surgical environment within the thoracic cavity "TC." Alternatively, and if desired, the retrieval bag 2 including the excised sample/specimen "S" may be removed from the thoracic cavity "TC" together. An advantage of withdrawing them together in some embodiments is that the outer bag can entrain the inner bag and aid the removal process as in certain instances it may be difficult to grasp the inner bag with enough purchase to apply sufficient retraction force.

The order or manner in which the retrieval bag 2 and "shrink-wrapped" portion of the retrieval bag 2 substantially around the excised sample/specimen "S" is removed from the thoracic cavity "TC" will depend on the specific surgical environment and/or other surgical parameters associated with a specific surgical procedure.

From the foregoing and with reference to the various figure drawings, those skilled in the art will appreciate that certain modifications can also be made to the present disclosure without departing from the scope of the same. For example, it is contemplated that the forceps 4 may be configured to directly couple to the retrieval bag 4. In this instance, a supply hose, e.g., a supply hose similar to that of supply house 31, is operably associated with the forceps 4 and the fluid circulator 6 and is configured to supply the evacuated air from the thoracic cavity "TC," to the retrieval bag 2. In this instance, the previously described configuration of lumen 28 and hub 29 associated with the forceps 4 may be configured accordingly.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for removing tissue from a body cavity of a patient, the method comprising:
   forming at least one incision in tissue to access the body cavity;
   inserting a retrieval bag though the at least one incision and into the body cavity adjacent a tissue specimen;

evacuating gaseous matter from the body cavity and inflating the retrieval bag with the evacuated gaseous matter such that the retrieval bag substantially encircles the tissue specimen;

substantially sealing a portion of the retrieval bag around the tissue specimen such that the substantially sealed portion of the retrieval bag is separated from the rest of the retrieval bag; and removing the substantially sealed portion of the retrieval bag including the tissue specimen contained therein from the body cavity.

2. A method according to claim 1, further comprising the step of removing the remainder of the retrieval bag from the body cavity.

3. A method according to claim 1, wherein the step of substantially sealing a portion of the retrieval bag includes inserting a sealing instrument into the retrieval bag.

4. A method according to claim 3, wherein the step of substantially sealing a portion of the retrieval bag further includes the step of translating a cutting element through the sealed portion of the retrieval bag.

5. A method according to claim 1, wherein prior to the step of inserting the retrieval bag, the tissue specimen is excised.

6. A method according to claim 5, wherein the step of excising the tissue specimen includes excising tissue that is located within a thoracic cavity of a patient.

7. A method according to claim 1, wherein the step of inserting the retrieval bag includes inserting a retrieval bag that is made from an elastomeric bio-compatible material.

8. A method according to claim 1, wherein the step of evacuating gaseous matter includes the step of introducing a surgical instrument that is operably associated with a fluid circulator and in fluid communication with the retrieval bag into the incision that is not occupied by the retrieval bag.

9. A method according to claim 1, wherein the step of inserting the retrieval bag includes inserting a retrieval bag that includes a textured surface, wherein the textured surface is configured to facilitate maintaining the tissue specimen in a substantially fixed position during the evacuation step.

10. A method according to claim 1, wherein the step of removing the substantially sealed portion includes removing the rest of the retrieval bag including the substantially sealed portion of the retrieval bag including the tissue specimen contained therein simultaneously from the body cavity.

11. A system configured for removing tissue from a body cavity, comprising:

a retrieval bag insertable through a first incision in tissue, the retrieval bag including an open end and a closed end;

a surgical instrument insertable into the body cavity and configured to grasp and excise a tissue specimen from within the body cavity and selectively substantially seal the retrieval bag; and a fluid circulator in fluid communication with the surgical instrument and the open end of the retrieval bag, the fluid circulator configured to evacuate gaseous matter from within the body cavity and into the open end of the retrieval bag such that the retrieval bag substantially encircles the excised tissue specimen.

12. A system according to claim 11, wherein the retrieval bag is made from an elastomeric bio-compatible material.

13. A system according to claim 11, wherein the retrieval bag includes a textured surface, wherein the textured surface is configured to facilitate maintaining the tissue specimen in a substantially fixed position during the evacuation of gaseous matter from within the body cavity.

14. A system according to claim 11, wherein the surgical instrument that is configured to grasp and excise a tissue specimen and the surgical instrument that is configured to selectively substantially seal the retrieval bag are the same surgical instrument.

15. A system according to claim 14, wherein one of the surgical instrument and fluid circulator is in fluid communication with the retrieval bag via a fluid conduit.

16. A system according to claim 14, wherein the surgical instrument is an endoscopic forceps.

17. A system according to claim 16, wherein the instrument includes a cutting element that is configured to excise the tissue specimen, and sever the retrieval bag subsequent to the placing of the tissue specimen therein and the sealing thereof.

18. A system according to claim 16, wherein seal surfaces that are associated with the forceps include a lubricious coating that is configured to facilitate sealing of the retrieval bag.

19. A system according to claim 11, wherein the surgical instrument is insertable through a second incision in tissue.

* * * * *